US006242246B1

(12) United States Patent
Gold et al.

(10) Patent No.: US 6,242,246 B1
(45) Date of Patent: Jun. 5, 2001

(54) NUCLEIC ACID LIGAND DIAGNOSTIC BIOCHIP

(75) Inventors: Larry Gold; Dan Drolet; Dom Zichi; Sumedha Jayasena, all of Boulder; Steve Creighton, Denver; Stanley Gill, Boulder, all of CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 08/990,436

(22) Filed: Dec. 15, 1997

(Under 37 CFR 1.47)

(51) Int. Cl.$^7$ .............................. C12M 1/36; C12P 19/34; C12Q 1/68; C07H 21/04
(52) U.S. Cl. ..................................... 435/287.1; 435/287.2; 435/91.1; 435/6; 435/194; 536/24.3; 536/23.1; 536/25.4
(58) Field of Search .............................. 435/287.1, 287.2, 435/91.1, 6, 194; 436/94; 536/24.3, 23.1, 25.4

(56) References Cited

U.S. PATENT DOCUMENTS

| 4,562,157 | 12/1985 | Lowe et al. ........................ 435/291 |
| 5,270,163 | * 12/1993 | Gold et al. ............................. 435/6 |
| 5,412,087 | 5/1995 | McGall et al. ...................... 536/24.3 |

(List continued on next page.)

FOREIGN PATENT DOCUMENTS

WO95/18377   7/1995   (WO) .

OTHER PUBLICATIONS

Szostak, "Structure and Activity of Ribozymes," in *Redesigning the Molecules of Life*, (S.A. Benner ed.) Springer–Verlag Berlin Heidelberg, pp. 87–113, (1988).

Lipshutz et al. (1995) BioTechniques 19:442.

Kleinjung et al. (1998) *Analytical Chemistry* 70:328–331.

*Primary Examiner*—Stephanie Zitomer
*Assistant Examiner*—B J Forman
(74) *Attorney, Agent, or Firm*—Swanson & Bratschun LLC

(57) ABSTRACT

A Nucleic acid ligand "Biochip" is disclosed, consisting of a solid support to which one or more specific Nucleic acid ligands is attached in a spatially defined manner. Each Nucleic acid ligand binds specifically and avidly to a particular Target molecule contained within a Test mixture, such as a Bodily fluid The Target molecules include, but are not limited to, proteins (cellular, viral, bacterial, etc.) hormones, sugars, metabolic byproducts, cofactor, and intermediates, drugs, and toxins. Contacting the Test mixture with the Biochip leads to the binding of a Target molecule to its cognate Nucleic acid ligand. Binding of Target to the Nucleic acid ligand results in a detectable change at each specific location on the Biochip. The detectable change can include, but is not limited to, a change in fluorescence, or a change in a physical parameter, such as electrical conductance or refractive index, at each location on the Biochip. The Biochip will then be read by a device, such as a fluorescence scanner or a surface plasma resonance detector, that can measure the magnitude of the change at each location on the Biochip. The location of the change reveals what Target molecule has been detected, and the magnitude of the change indicates how much of it is present The combination of these two pieces of information will yield diagnostic and prognostic medical information when signal patterns are compared with those obtained from Bodily fluids of individuals with diagnosed disorders FIG. 1). In principle, the Biochip could be used to test any chemically complex mixture provided that Nucleic acid ligands to components suspected of being present in the mixture are attached to the Biochip. Thus, the Nucleic acid ligand Biochip will have a wider use in environmental testing, etc.

4 Claims, 6 Drawing Sheets

U.S. PATENT DOCUMENTS

| | | |
|---|---|---|
| 5,432,099 | 7/1995 | Ekins et al. .......................... 436/518 |
| 5,445,934 | 8/1995 | Fodor et al. ............................. 435/6 |
| 5,510,270 | 4/1996 | Fodor et al. ........................ 436/518 |
| 5,556,752 | 9/1996 | Lockhart et al. ........................ 435/6 |
| 5,582,981 * | 12/1996 | Toole et al. .............................. 435/6 |
| 5,599,720 | 2/1997 | Ekins et al. .......................... 436/501 |
| 5,688,935 | 11/1997 | Stephens et al. ................... 536/23.1 |
| 5,744,305 | 4/1998 | Fodor et al. ............................. 435/6 |
| 5,861,254 | 1/1999 | Schneider et al. ...................... 435/6 |

* cited by examiner

NUCLEIC ACID LIGAND DIAGNOSTIC BIOCHIP

FIELD OF THE INVENTION

The invention is directed to methods for the detection of target molecules in test solutions, particularly medically relevant molecules contained in Bodily fluids. The methods described herein use specific Nucleic acid ligands attached to solid supports at spatially discrete locations. The invention provides methods for detecting the binding of target molecules to Nucleic acid ligands, and methods for using arrays of Nucleic acid ligands in diagnostic medical applications.

BACKGROUND OF THE INVENTION

A method for the in vitro evolution of Nucleic acid molecules with highly specific binding to target molecules has been developed. This method, Systematic Evolution of Ligands by Exponential Enrichment, termed the SELEX process, is described in U.S. patent application Ser. No. 07/536,428, entitled "Systematic Evolution of Ligands by Exponential Enrichment", now abandoned, U.S. patent application Ser. No. 07/714,131, filed Jun. 10, 1991, entitled "Nucleic Acid Ligands", now U.S. Pat. No. 5,475,096, U.S. patent application Ser. No. 07/931,473, filed Aug. 17, 1992, entitled "Methods for Identifying Nucleic Acid Ligands", now U.S. Pat. No. 5,270,163 (see also WO91/19813), each of which is herein specifically incorporated by reference. Each of these applications, collectively referred to herein as the SELEX Patent Applications, describes a fundamentally novel method for making a Nucleic acid ligand to any desired target molecule.

The SELEX method involves selection from a mixture of candidate oligonucleotides and stepwise iterations of binding, partitioning and amplification, using the same general selection scheme, to achieve virtually any desired criterion of binding affinity and selectivity. Starting from a mixture of Nucleic acids, preferably comprising a segment of randomized sequence, the SELEX method includes steps of contacting the mixture with the target under conditions favorable for binding, partitioning unbound Nucleic acids from those Nucleic acids which have bound specifically to target molecules, dissociating the Nucleic acid-target complexes, amplifying the Nucleic acids dissociated from the Nucleic acid-target complexes to yield a ligand-enriched mixture of Nucleic acids, then reiterating the steps of binding, partitioning, dissociating and amplifying through as many cycles as desired to yield highly specific, high affinity Nucleic acid ligands to the target molecule.

The SELEX method encompasses the identification of high-affinity Nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic acid ligands containing modified nucleotides are described in U.S. patent application Ser. No. 08/117,991, filed Sep. 8, 1993, entitled "High Affinity Nucleic Acid Ligands Containing Modified Nucleotides", that describes oligonucleotide containing nucleotide derivatives chemically modified at the 5- and 2'-positions of pyrimidines. U.S. patent application Ser. No. 08/134,028, supra, describes highly specific Nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement", describes oligonucleotide containing various 2'-modified pyrimidines.

Given the remarkable ability of Nucleic acid ligands to be generated against many different target molecules, it would be desirable to have methods for using said ligands as a diagnostic tool. In particular, it would be desirable to attach a plurality of different Nucleic acid ligands to a microfabricated solid support (a "Biochip"), and then assay the binding to said ligands of target molecules in a Bodily fluid. The subject application provides such methods.

SUMMARY OF THE INVENTION

Methods are provided in the instant invention for obtaining diagnostic and prognostic Nucleic acid ligands, attaching said ligands to a Biochip, and detecting binding of target molecules in a Bodily fluid to said Biochip-bound Nucleic acid ligands. In one embodiment of the instant invention, one or more Nucleic acid ligands are chosen that bind to molecules known to be diagnostic or prognostic of a disease; these ligands are then attached to the Biochip. Particular methods for attaching the Nucleic acid ligands to the Biochip are described below in the section entitled "Fabrication of the Nucleic Acid Biochip". The Biochip may comprise either (i) Nucleic acid ligands selected against a single target molecule; or more preferably, (ii) Nucleic acid ligands selected against multiple target molecules. In the subject invention, the level of target molecule binding to Nucleic acid ligands at defined spatial locations will be determined using Bodily fluid from individuals known to have the disease for which that target molecule is known to be prognostic or diagnostic, and also using Bodily fluid from healthy individuals. Bodily fluid from an individual seeking a prognostic report can then be assayed using the Biochip, and comparison of the three sets of data will yield prognostic or diagnostic information for that individual.

In another embodiment, the specific Nucleic acid ligands attached to the Biochip bind specifically to all or a large number of components of blood plasma, or other Bodily fluids, of a healthy individual. The pattern and level of binding of these ligands to their targets will then be determined by the methods disclosed below for healthy individuals, and also for individuals diagnosed with various medical conditions. A computer database of Biochip binding data will then be established, with each disease giving rise to a unique "signature" binding pattern Bodily fluids from individuals desiring a prognostic or diagnostic report will then be contacted with the Biochip, and the binding pattern obtained compared with the reference database.

In a related embodiment, the attached Nucleic acid ligands will bind specifically to all or a large number of components of the blood plasma, or other Bodily fluid, of an individual known to be suffering from a particular disease. Once the pattern and level of target molecule binding to this Biochip has been determined for the individual suffering from the disease, this Biochip can be used to screen individuals known to be at risk of developing this disease. This embodiment will be useful for diseases in which the target molecules are not found in the Bodily fluid of healthy individuals, and the target molecules themselves are not yet identified (e.g., for viral, bacterial or parasitic infections where the causative agent has not yet been characterized at the molecular level).

In all the methods described in this invention, it is not necessary to know what each Nucleic acid ligand is binding.

The preceding two embodiments are particularly preferred, as they will allow for the early diagnosis of diseases for which there are no currently known assays, and for which diagnosis traditionally depends on the manifestation of overt disease symptoms. It will then be possible to identify the Nucleic acid ligands that are binding target molecules of relevance, and thereby identify those target molecules. These embodiments will greatly expedite research into disease, and will provide many new target molecules that can be used in directed diagnostic and drug discovery programs. Furthermore, the Nucleic acid ligands identified on the Biochip that bind to these target molecules may themselves have potential for use as therapeutic agents.

In the most preferred embodiment, the Biochip contains both types of Nucleic is acid ligands described in the previous two embodiments. Such a Biochip will be able to detect or predict diseases where the diagnostic or prognostic criterion is (i) a change in the concentration of molecule(s) normally found in Bodily fluid; and/or (ii) the presence of a molecule not normally found in a Bodily fluid of a healthy individual, e.g., a viral protein. FIG. 1 shows the use of such a Biochip. For the sake of clarity, only a simple 4×4 array is illustrated; typical embodiments may use arrays that are 100×100 or greater.

DETAILED DESCRIPTION OF THE INVENTION

Contents

Figure 1:
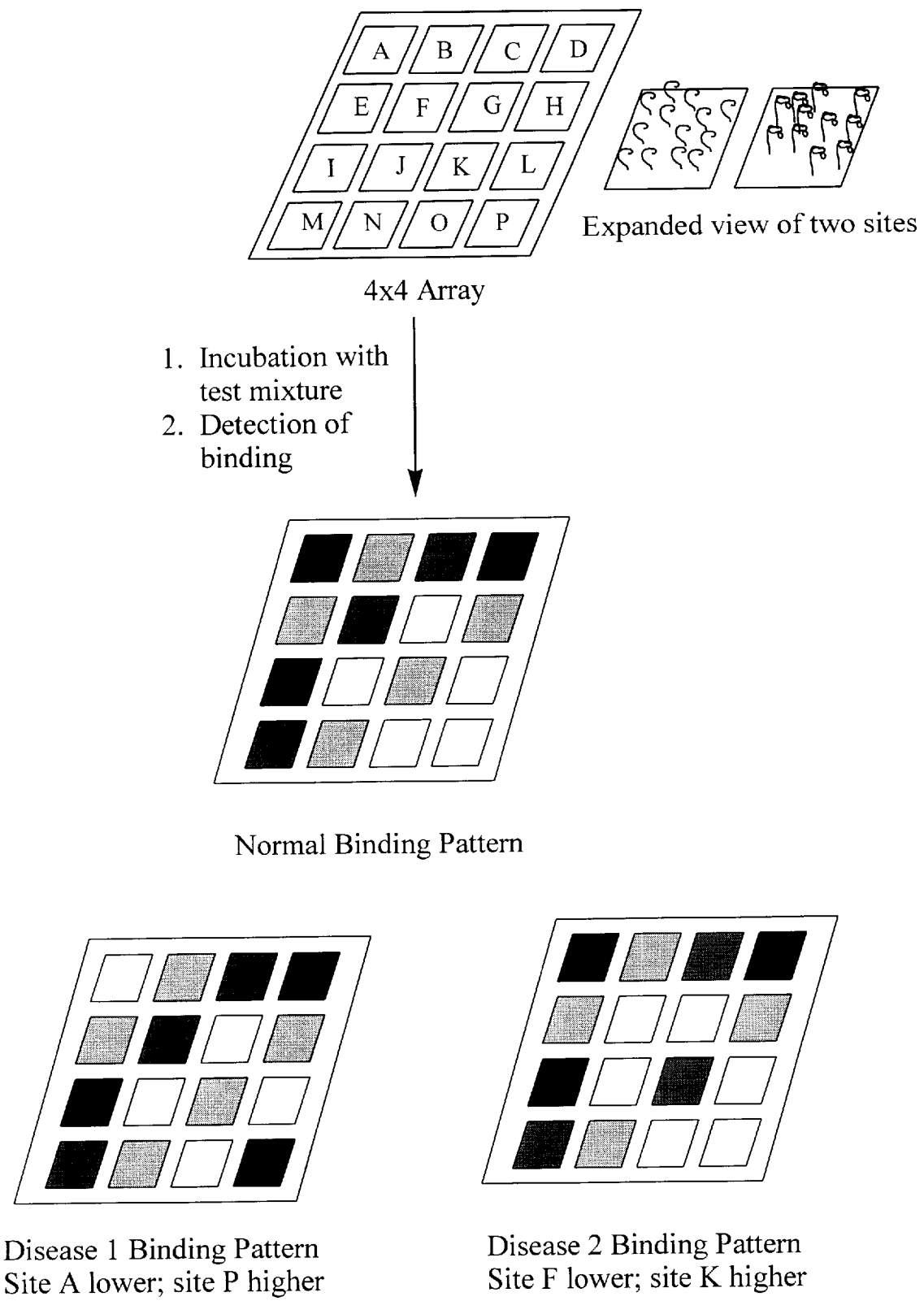
FIG. 1 shows the use of a patterned array of Nucleic acid ligands. Contacting the Biochip with a Test mixture results in a binding pattern that can be used to diagnose or predict disease.

I. Glossary
II. Obtaining Nucleic Acid Ligands For Use on a Biochip
III. Fabrication of the Nucleic Acid Ligand Biochip
IV. Detection of Target Molecule Binding to Nucleic Acid Ligand Using Fluorescence Techniques
  A. Generic Detection Techniques
  B. Detection Using an Oligonucleotide with Sequence Complementary to the Nucleic Acid Ligand
  C. Incorporation of Small Molecule Binding Sites into Nucleic Acid Ligands to Facilitate Detection of Target Molecule Binding
  D. Detection Through a Hybridization Cascade
  E. Direct Binding of Target Molecules to Spectroscopically Detectable Nucleic Acid Ligands
  F. Detection of Changes in Double-Helicity Accompanying Target Binding
  G. Detection through the use of Interferometry
  H. Detection of Covalently-Bound Target Molecules
V. Detection of Target Molecule Binding Through Methods That Do Not Involve Fluorescence
  A. Chemical Field Effect Transistors
  B. Detection Through Surface Plasma Resonance
  C. Detection Through the Use of Mass Spectroscopy
  D. Detection Through Atomic Force Microscopy (AFM) and Scanning-Tunneling Microscopy (STM)
VI. Examples

I. Glossary

The following terms are intended to have the following general meanings as they are used herein:

1. "SELEX" methodology refers to the combination of selection of nucleic acid ligands which interact with a target in a desirable manner, for example binding to a protein, with amplification of those selected nucleic acids as described in detail above and in the SELEX patent applications. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved.

2. "SELEX Target" or "Target molecule" or "Target" refers herein to any compound upon which a Nucleic acid can act in a predetermined desirable manner. A SELEX target molecule can be a protein, peptide, Nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, Tissue, etc., without limitation. Virtuly any chemical or biological effector would be a suitable SELEX target. Molecules of any size can serve as SELEX targets. A target can also be modified in certain ways to enhance the likelihood of an interaction between the target and the Nucleic acid.

3. "Tissue target" or "Tissue" refers herein to a certain subset of the SELEX Targets described above. According to this definition, Tissues are macromolecule in a heterogeneous environment As used herein, Tissue refers to a single cell type, a collection of cell types, an aggregate of cells, or an aggregate of macromolecule. This differs from simpler SELEX Targets which are typically isolated soluble molecules, such as proteins. In the preferred embodiment, Tissues are insoluble macromolecules which are orders of magnitude larger than simpler SELEX Targets. Tissues are complex Targets made up of numerous macromolecules, each macromolecule having numerous potential epitopes. The different macromolecule which comprise the numerous epitopes can be proteins, lipids, carbohydrates, etc., or combinations thereof. Tissues are generally a physical array of macromolecules that can be either fluid or rigid, both in terms of structure and composition. Extracellular matrix is an example of a more rigid Tissue, both structurally and compositionally, while a membrane bilayer is more fluid in structure and composition. Tissues are generally not soluble and remain in solid phase, and thus partitioning can be accomplished relatively easily. Tissue includes, but is not limited to, an aggregate of cells usually of a particular kind together with their intercellular substance that form one of the structural materials commonly used to denote the general cellular fabric of a given organ, e.g., kidney Tissue, brain Tissue. The four general classes of Tissues are epithelial Tissue, connective Tissue, nerve Tissue, and muscle Tissue.

Examples of Tissues which fall within this definition include, but are not limited to, heterogeneous aggregates of macromolecule such as fibrin clots which are acellular, homogeneous or heterogeneous aggregates of cells; higher ordered structures containing cells which have a specific function, such as organs, tumors, lymph nodes, arteries, etc.; and individual cells. Tissues or cells can be in their natural environment, isolated, or in Tissue culture. The Tissue can be intact or modified. The modification can include numerous changes such as transformation, transfection, activation, and substructure isolation, e.g., cell membranes, cell nuclei, cell organelles, etc.

Sources of the Tissue, cell or subcellular structures can be obtained from prokaryotes as well as eukaryotes. This includes human, animal, plant, bacterial, fungal and viral structures.

4. "Nucleic acid" means either DNA, RNA, single-stranded or double-stranded and any chemical modifications thereof Modifications include, but are not limited to, those which provide other chemical groups that incorporate additional charge, polarizability, hydrogen bonding, electrostatic interaction, and fluxionality to the individual Nucleic acid bases or to the Nucleic acid as a whole. Such modifications include, but are not limited to, modified bases such as 2'-position sugar modifications, 5-position pyrimidine modifications, 8-position purine modifications, modifications at cytosine exocyclic amines, substitution of 5-bromo-uracil; backbone modifications, methylations, unusual base-pairing combinations such as the isobases isocytidine and isoguanidine and the like. Modifications can also include 3' and 5' modifications such as capping. Modifications that occur after each round of amplification are also compatible with this invention. Post-amplification modifications can be reversibly or irreversibly added after each round of amplification. Virtually any modification of the Nucleic acid is contemplated by this invention.

5. "Nucleic acid Test mixture" or "Nucleic acid candidate mixture" refers herein to a mixture of Nucleic acids of differing, randomized sequence. The source of a "Nucleic acid Test mixture" can be from naturally-occurring Nucleic acids or fragments thereof, chemically synthesized Nucleic acids, enzymatically synthesized Nucleic acids or Nucleic acids made by a combination of the foregoing techniques. In a preferred embodiment, each Nucleic acid has fixed sequences surrounding a randomized region to facilitate the amplification process. The length of the randomized section of the Nucleic acid is generally between 8 and 250 nucleotides, preferably between 8 and 60 nucleotides.

6. "Nucleic acid ligand" refers herein to a Nucleic acid which has been isolated from the Nucleic acid candidate mixture that acts on a Target in a desirable manner. Examples of actions on a Target in a desirable manner include, but are not limited to binding of the Target, catalytically changing the Target, reacting with the Target in a way which modifieslalters the Target or the functional activity of the Target, covalently attaching to the Target as in a suicide inhibitor, facilitating the reaction between the Target and another molecule. In most, but not all, instances this desirable manner is binding to the Target In the most preferred embodiment, a Nucleic acid ligand is a non-naturally occurring Nucleic acid sequence having a specific binding affinity for a Target molecule, such Target molecule being a three dimensional chemical structure other than a polynucleotide that binds to said Nucleic acid ligand through a mechanism which predominantly depends on Watson/Crick base pairing or triple helix binding, wherein said Nucleic acid ligand is not a Nucleic acid having the known physiological function of being bound by the Target molecule. Nucleic acid ligand includes Nucleic acid sequences that are substantially homologous to the Nucleic acid ligands actually isolated by the SELEX procedures. By substantially homologous it is meant a degree of primary sequence homology in excess of 70%, most preferably in excess of 80%. In the past it has been shown that various Nucleic acid ligands to a specific Target with little or no primary homology may have substantially the same ability to bind the Target For these reasons, this invention also includes Nucleic acid ligands that have substantially the same ability to bind a Target as the Nucleic acid ligands identified by the SELEX process. Substantially the same ability to bind a Target means that the affinity is within a few orders of magnitude of the affinity of the ligands described herein. It is well within the skill of those of ordinary skill in the art to determine whether a given sequence—substantially homologous to those specifically described herein—has substantially the same ability to bind a Target.

7. "Bodily fluid" refers herein to a mixture of macromolecules obtained from an organism. This includes, but is not limited to, blood plasma, urine, semen, saliva, lymph fluid, meningal fluid, amniotic fluid, glandular fluid, and cerebrospinal fluid. This also includes experimentally separated fractions of all of the preceding. "Bodily fluid" also includes solutions or mixtures containing homogenized solid material, such as feces, Tissues, and biopsy samples.

8. "Test mixture" refers herein to any sample that contains a plurality of molecules, the identity of at least some of which can be detected using a Nucleic acid ligand Biochip. This includes, but is not limited to, Bodily fluids as defined above, and any sample for environmental and toxicology testing such as contaminated water and industrial effluent 9. "Biochip" is any microfabricated solid surface to which molecules may be attached through either covalent or non-covalent bonds. This includes, but is not limited to, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is contemplated. This includes planar surfaces, and also spherical surfaces.

II. Obtaining Nucleic Acid Ligands For Use on a Biochip

The basic SELEX method has been modified to achieve a number of specific objectives. For example, U.S. patent application Ser. No. 08/123,935, filed Sep. 17, 1993, entitled "Photoselection of Nucleic Acid Ligands" describes a SELEX based method for selecting Nucleic acid ligands containing photoreactive groups capable of binding and/or photo crosslinking to and/or photo inactivating a Target molecule. U.S. patent application Ser. No. 08/134,028, filed Oct. 7, 1993, entitled "High-Affinity Nucleic Acid Ligands That Discriminate Between Theophylline and Caffeine", describes a method for identifying highly specific Nucleic acid ligands able to discriminate between closely related molecules, termed Counter-SELEX U.S. patent application Ser. No. 08/143,564, filed Oct. 25, 1993, entitled "Systematic Evolution of Ligands by EXponential Enrichment: Solution SELEX", describes a SELEX-based method which achieves highly efficient partitioning between oligonucleotide having high and low afmity for a Target molecule. U.S. patent application Ser. No. 08/442,062, filed May 16 1995, entitled "Methods of Producing Nucleic Acid Ligands", now U.S. Pat. No. 5,595,877 describes methods for obtaining improved Nucleic acid ligands after SELEX has been performed. U.S. patent application Ser. No. 08/400,440, filed Mar. 8, 1995, entitled "Systematic Evolution of Ligands by EXponential Enrichment: Chemi-SELEX", describes methods for covalently linking a ligand to its Target Of particular note to the instant application, U.S. patent application Ser. No. 08/434,425, filed May 3, 1995 entitled "Tissue SELEX" describes methods for identifying and preparing Nucleic acid ligands against an entire Tissue, wherein Tissue is defined as a single. cell type, a collection of cell types, an aggregate of cells or an aggregate of macromolecules. Examples of candidate Tissues include tumors and blood plasma These methods are also disclosed in great details in U.S. patent application Ser. Nos. 08/434,425, 08/437,667, 08/434,001, 08/433,585, 08/906,955, 08/433,124, and 08/433,126.

The SELEX method encompasses combining selected oligonucleotide with other selected oligonucleotide and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459, and U.S. patent application Ser. No. 08/234,997, filed Apr. 28, 1994, entitled "Systematic Evolution of Ligands by Exponential Enrichment: Blended SELEX", respectively. These applications allow the combination of the broad array of shapes and other properties, and the efficient amplification and replication properties, of oligonucleotide with the desirable properties of other molecules. Each of the above described patent applications which describe modifications of the basic SELEX procedure are specifically incorporated by reference herein in their entirety. Any variation of the SELEX method that allows for the incorporation of a detectable group (such as a fluorescent chemical, or a group such as digoxigenin that is recognized by an antibody), an affinity group (such as biotin), a reactive group (such as a photoreactive group or a chemical group that permits attached of the ligand to a Biochip surface), or of the binding site sequence of another SELEX Target is also contemplated in the subject invention.

In a preferred embodiment, the SELEX procedure is carried out in the presence of blood plasma in order ultimately to obtain Nucleic acid ligands that bind the Target molecule specifically without the possibility that they cross react with other molecules in plasma. Some examples of Nucleic acid ligands that have utility in the Biochip include, but are not limited to, ligands against HIV-1 tat protein (U.S. Pat. Nos. 5,527,894 and 5,637,461), HIV-1 gag (U.S. patent application Ser. No. 08/447,172), HIV-1 integrase (U.S. Pat. No. 5,587,468), HIV-1 nucleocapsid components (U.S. Pat. Nos. 5,654,151 and 5,635,615) HIV-1 reverse transcriptase (U.S. Pat. Nos. 5,496,938 and 5,5,03,978), thrombin (U.S. Pat. Nos. 5,476,766 and 5,543,293), basic fibroblast growth factor (U.S. Pat. Nos. 5,459,015 and 5,639,868), vascular endothelial growth factor (U.S. patent application Ser. No. 08/447,169), insulin receptor antibodies (U.S. patent application Ser. No. 08/248,632, now abandoned), the tachykinin substance P (U.S. Pat. Nos. 5,648,214 and 5,637,682), immunoglobulin E (U.S. Pat. Nos. 5,629,155 and 5,686, 592), secretory phospholipase $A_2$ (U.S. Pat. No. 5,622,828), TGFb (U.S. patent application Ser. No. 08/458,423 and 08/458,424), platelet derived growth factor U.S. Pat. No. 5,668,264, U.S. patent application Ser. No. 08/618,693 and World patent application PCT/US96/08014), human kerotinocyte growth factor (World patent application PCTIUS96/08014, U.S. patent application Ser. No. 08/465,594), chorionic gonadotropin (U.S. patent application Ser. No. 08/488, 402 and 08/484,552), lectins (U.S. patent application Ser. No. 08/479,724, 08/477,829 and 08/472,256) cytokines (U.S. patent application Ser. No. 08/477,527 and 08/481, 710), lupus antibodies (U.S. patent application Ser. No. 08/520,932), and complement system proteins (U.S. patent application Ser. No. 08/595,335).

As described in the SELEX patent applications, it is possible to create Nucleic acid ligands with constant and random sequence regions. In a particularly preferred embodiment, Nucleic acid ligands will be synthesized that have a common short sequence (seq. A) located at a predetermined position. The initial candidate mixture of Nucleic acids will then be contacted with a solid support, preferably a column, containing an immobilized Nucleic acid (seq. A') complementary in sequence to the common short sequence on each ligand. The pool of ligands will then bind to the column through complementary base pairing between A and A'. A mixture containing the Target molecule(s) will then be passed over the column, and ligands that are displaced from the column will be collected. The displacement of these ligands indicates that the binding of the Target molecule alters the conformation of the ligand in such a manner that the common short sequence is no longer able to bind to its complementary sequence. In a related embodiment, the initial candidate mixture of Nucleic acid ligands will be contacted with Target molecule, and binding will be allowed to occur in solution phase. The Nucleic acid ligands will then be contacted with the column described above. Nucleic acid ligands that have bound Target in such a way that sequence A is not able to hybridize to column-bound sequence A' will pass through the column, and can be collected. The Nucleic acid ligands obtained in these two embodiments will be used in the Biochip as described in detail below in the section entitled "Detection of Target Molecule Binding to Nucleic Acid Ligand Using Fluorescence Techniques".

One of the most powerful aspects of the present invention is the ability to identify an extremely large number of Nucleic acid ligands that recognize correspondingly large numbers of Targets in a biological sample. In many embodiments of the invention, the larger the number of Targets that are identifiable in a solution the better. The SELEX process allows for the selection of Nucleic acid ligands without knowing what molecular Target they bind to. For diagnostic and prognostic purposes, the specific Targets can be almost irrelevant as long some pattern of Target presence is indicative of a certain condition. By this process, it is likely that presence of multiple Targets, seemingly unrelated, would be determined to be diagnostic or prognostic of a given condition. This invention frees the investigator from having to determine which Targets to detect for within a given biological sample. Because SELEX can simultaneously identify ligands to huge numbers of epitopes within a complex sample, a new diagnostic approach can be employed that does not reply on a previous knowledge of which Targets are critical.

Thus, in certain aspects of the invention, the Biochip may be comprised of literally thousands of Nucleic acid ligands to indeterminate Targets. In other embodiments, the Targets for each attached Nucleic acid ligand may be either predetermined based on the nature of the SELEX protocol employed, or determined after the Nucleic acid ligand was identified.

III. Fabrication of the Nucleic Acid Ligand Biochip

The production of Biochips on which Nucleic acids are immobilized is well known in the art. The Biochip may be a Langmuir-Bodgett film, functionalized glass, germanium, silicon, PITE, polystyrene, gallium arsenide, gold, silver, or any other material known in the art that is capable of having functional groups such as amino, carboxyl, thiol or hydroxyl incorporated on its surface. Preferably, these groups are then covalently attached to crosslinking agents, so that the subsequent attachment of the Nucleic acid ligands and their interaction with Target molecules will occur in solution without hindrance from the Biochip. Typical crosslinking groups include ethylene glycol oligomer, diamines, and amino acids. Any suitable technique useful for immobilizing a Nucleic acid ligand to a Biochip is contemplated by this invention.

In one embodiment, one or more Nucleic acid ligands will be attached to the support by photolithography using a photoreactive protecting group on a coupling agent Such a technique is disclosed in McGall et al. U.S. Pat. No. 5,412, 087. Thiolpropionate having a photochemically removable protecting group is covalently coupled to functional groups on the surface of the Biochip. Light of the appropriate wavelength is then used to illuminate predefined regions of the surface, resulting in photo deprotection of the thiol group. A mask will be used to ensure that photo deprotection only takes place at the desired sites or addresses. Nucleic acid ligands containing thiol reactive groups, such as maleimides, are then attached to the deprotected regions. The unbound Nucleic acid ligand will then be washed away, and the process repeated at another location with another Nucleic acid ligand. A similar method uses a 5'-nitroveratryl protected thymidine linked to an aminated Biochip via a linkage to the 3'-hydroxyl group (Fodor et al. 1991, Science 251:767–773). Photo deprotection of the thymidine derivative allows a phosphoramidite activated monomer (or oligomer) to react at this site. Other methods use a photo-activatable biotin derivative to spatially localize avidin binding. The avidin, by virtue of its ability to bind more than one biotin group at a time, will in turn be used as a means for spatially localizing a biotin-linked Nucleic acid ligand to the Biochip (Barrett et al. U.S. Pat. No. 5,252,743 and PCT 91/07807). In principle, the photo deprotection of a caged binding agent could be used for any ligand-receptor pair where one member of the. pair is a small molecule capable of being protected by a photolabile group. Other examples of such ligand-receptor pairing include mannose and concanavalin A, cyclic AMP and anti-cAMP antibodies, and tetrahydrofolate and folate binding proteins (U.S. Pat. No. 5,252,743).

In another embodiment, the regions of the Biochip that come into contact with the Nucleic acid ligand at each attachment photoactivation step are spatially restricted. This may be done by placing the support on a block containing channels through which the Nucleic acid ligand will be pumped, with each channel giving the Nucleic acid ligand access to only a small region of the Biochip. This prevents accidental binding of Nucleic acid ligand to non-photoactivated regions. Furthermore, it will be used to permit the simultaneous attachment of several different Nucleic acid ligands to the support. In this embodiment, a mask allows for the patterned illumination and consequent photoactivation of several regions of the Biochip at the same time. If the area surrounding each photoactivated region is segregated from the neighboring region by the aforementioned channel, then different Nucleic acid ligands will be delivered to these photoactivated regions by pumping each Nucleic acid ligand through a different channel (Winkler et al., U.S. Pat. No. 5,384,261).

The photoactivated regions in the methods described above will be at least as small as 50 $mm^2$. It has been shown that >250,000 binding sites per square centimeter is easily achievable with visible light; the upper limit is determined only by the diffraction limit of light (Fodor et al. 1991, Science 251:767–773). Therefore, photoactivation using electromagnetic radiation of a shorter wavelength will be used to generate correspondingly denser binding arrays. If the Biochip is transparent to the incident radiation it will be possible to simultaneously perform this process on a vertical stack of Biochips, greatly increasing the efficiency of Biochip production.

Alternatively, some form of template-stamping is contemplated, wherein a template containing the ordered array of Nucleic acid ligands (and possibly manufactured as described above) will be used to deposit the same ordered array on multiple Biochips.

In a further embodiment, the Nucleic acid ligand array will be formed on the Biochip by an "ink-jet" method, whereby the ligands are deposited by electro-mechanical dispensers at defined locations. An ink-jet dispenser capable of forming arrays of probes with a density approaching one thousand per square centimeter is described in Hayes et al. U.S. Pat. No. 5,658,802.

IV. Detection of Target Molecule Binding to Nucleic Acid Ligand Using Fluorescence Techniques
A. Generic Detection Techniques In one embodiment, protein Target molecules bound to Nucleic acid ligands on the surface of the Biochip will be detected by the addition of chemicals that non-specifically bind to all proteins. Any fluorescent chemical that is known in the art to bind proteins non-specifically will be suitable. Suitable examples include the dyes Nanorange and Cytoprobe, available from Molecular Probes, Inc.

In another embodiment, Target molecules bound to Nucleic acid ligands will be detected on the Biochip surface through the use of a sandwich assay. This method is well known to those skilled in the art. A sandwich assay uses antibodies that recognize specific bound Target molecules, preferably binding at a site distinct from that recognized by the Nucleic acid ligand. In such sandwich assays, the antibodies may be fluorescently labeled, or the bound antibodies may themselves be detected by contacting the Biochip with fluorescently labeled protein A, which binds all immunoglobulins. Alternatively, secondary antibodies specific for the immunoglobulin subtype of the first (primary) antibody will be contacted with the Biochip. The secondary antibodies may be fluorescently labeled, or they may be conjugated to a reporter enzyme, which enzyme catalyzes the production of a detectable compound. Sandwich assays have the potential to greatly amplify the detectable signal, in this case by the ability of the secondary antibody to bind to multiple sites on the primary antibody. All variations of the sandwich assay known in the art are contemplated in the subject invention.

In a related sandwich assay embodiment, the bound Target molecule will be detected by the use of a second Nucleic acid ligand, which binds to a site on the bound Target distinct from that recognized by the Biochip-bound Nucleic acid ligand As described in the paragraph above, the second Nucleic acid ligand may be fluorescently labeled, or it may be conjugated to biotin, allowing fluorescently labeled avidin, or an avidin conjugated reporter enzyme, to then bind to the bound second Nucleic acid ligand. Alternatively, the first and second Nucleic acid ligands may be labeled in an appropriate manner so that they form an energy transfer pair, as described below in the section entitled "Detection Using an Oligonucleotide with Sequence Complementary to the Nucleic Acid Ligand"

In another embodiment, Target molecule binding will be detected using a competition assay, well known to those skilled in the art. Following contacting of the Biochip-bound Nucleic acid ligands with the Test mixture, a solution containing a predetermined amount of each Target for which binding data is sought is added. These Target molecules are fluorescently labeled by any of the ways known in the art in order to permit their detection. The labeled Target molecules compete for binding to the immobilized Nucleic acid ligand. An equilibrium will be established, and the amount of labeled molecule bound at each site will be used to calculate the amount of each Target molecule contained within the original Test mixture.

Figure 2:
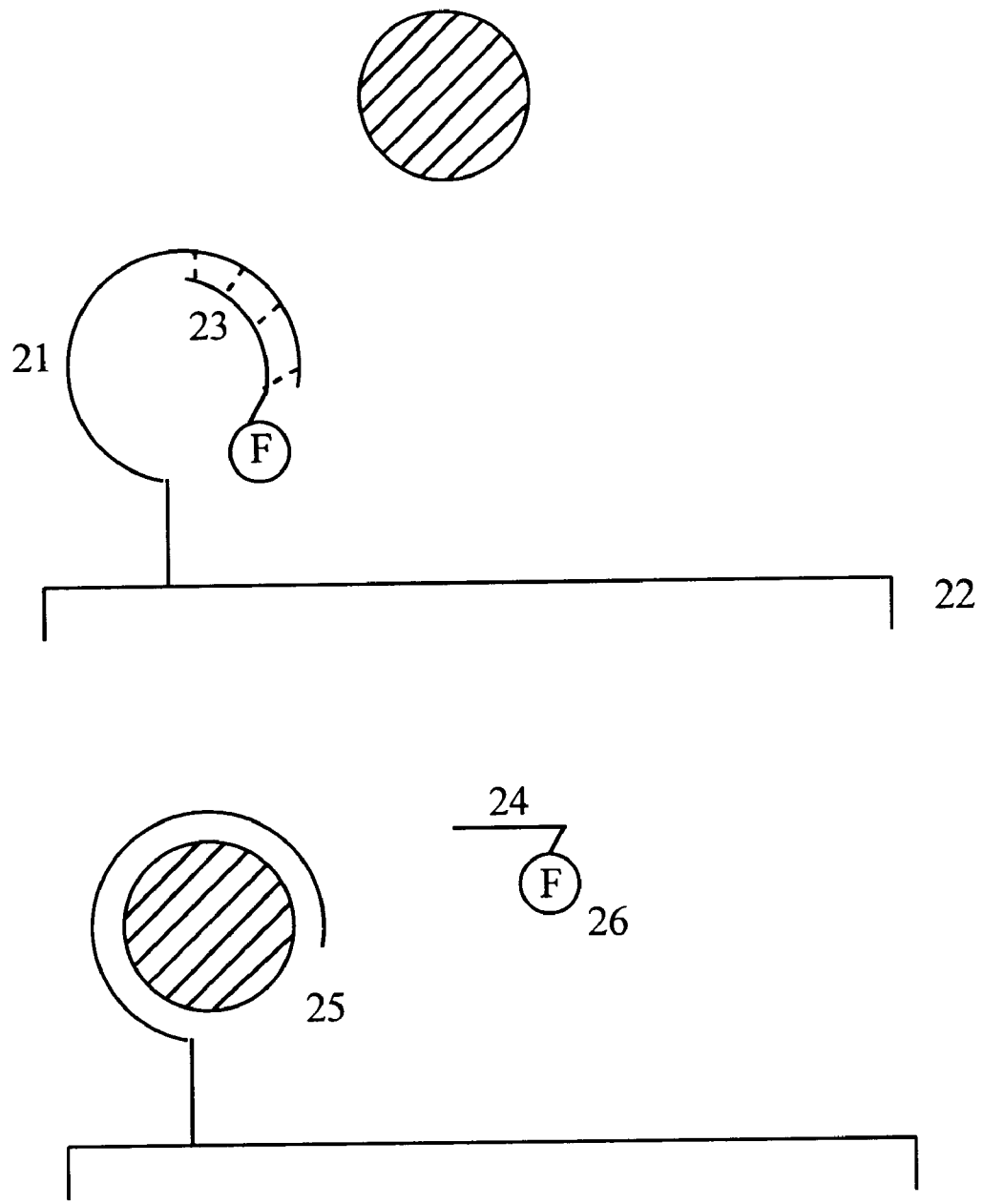
FIG. 2 depicts a mechanism for detection in which an oligonucleotide, complementary in sequence to all or part of the Nucleic acid ligand, is displaced from the Nucleic acid ligand by binding of the target molecule.
Figure 3:
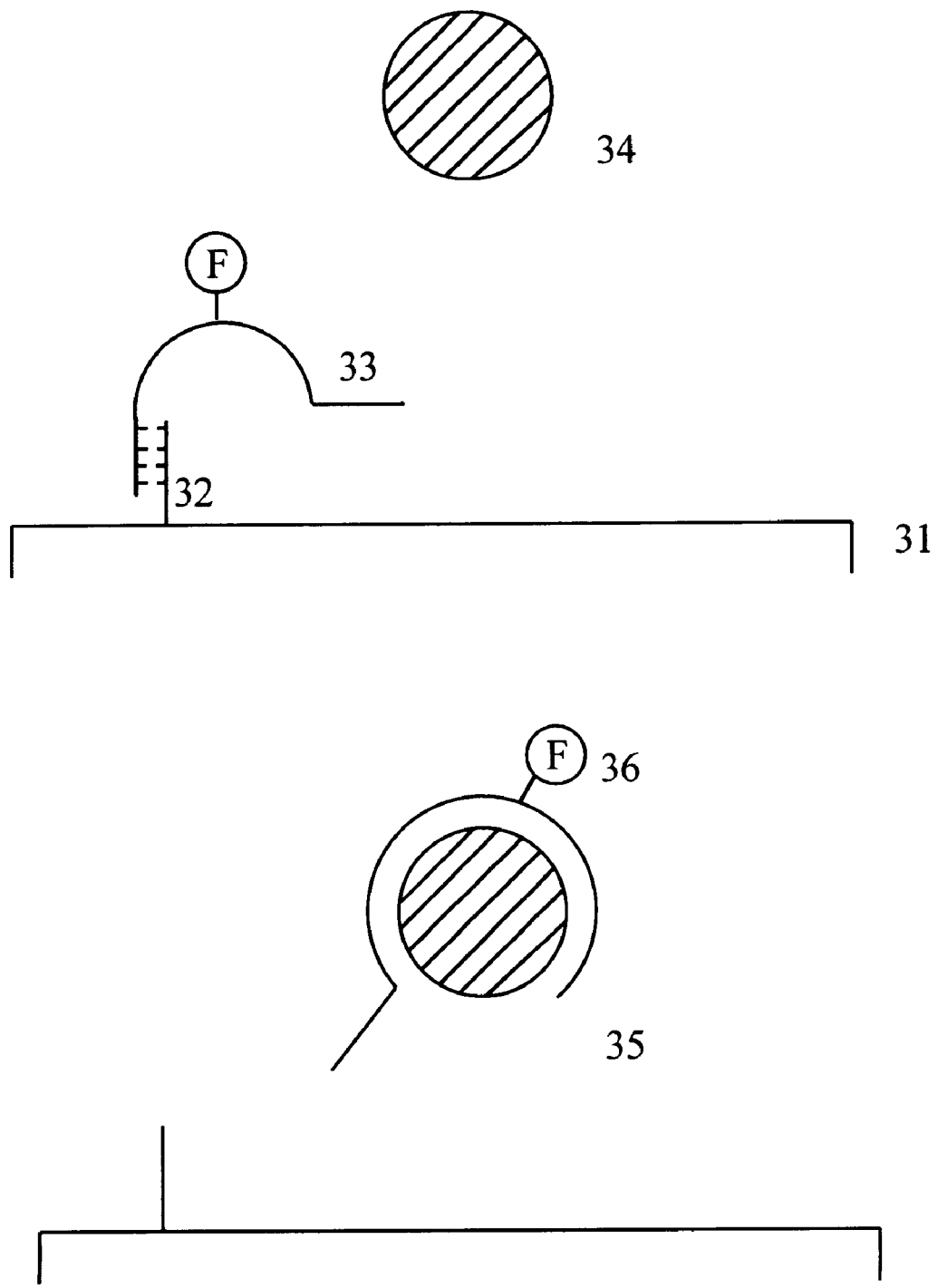
FIG. 3 illustrates a mechanism for detection in which a Nucleic acid ligand is bound to the Biochip via its interaction with an oligonucleotide, which oligonucleotide is covalently attached to the Biochip, and has a sequence complementary to all or part of the sequence of the Nucleic acid ligand.

B. Detection Using an Oligonucleotide with Sequence Complementary to the Nucleic Acid Ligand In certain preferred embodiments (FIG. 2), Nucleic acid ligands (21) containing a constant sequence associated with the binding site for the Target molecule will be localized to specific regions of a Biochip (22). The synthesis of such Nucleic acid ligands is described above in the section entitled "Obtaining Nucleic Acid Ligands For Use on a Biochip". The Biochip-bound Nucleic acid ligands will then be hybridized with an oligonucleotide (23) complementary in sequence to the constant region. Contacting this Biochip with a Test mixture will lead to displacement (24) of oligonucleotide from Nucleic acid ligands that bind to their Target molecule (25). In a further embodiment (FIG. 3), a Biochip (31) will be synthesized upon which the complementary oligonucleotide (32) is immobilized by any of the methods known in the art. The Nucleic acid ligands (33) will then be deposited at specific locations on the Biochip, whereupon they will become associated with the oligonucleotide by base pairing. The Biochip will then be contacted with the Test mixture. Target molecule binding (34) will lead to the disruption of base paring between the Nucleic acid ligand and the support bound oligonucleotide (35), and hence displacement of the Nucleic acid ligand from the Biochip will occur.

In the preceding embodiments, the displaced Nucleic acid is labeled (26,36) with fluorescein, tetramethylrhodamine, Texas Red, or any other fluorescent molecule known in the art, leading to a decrease in fluorescence intensity at the site of Target molecule binding. The level of label detected at each address on the Biochip will then vary inversely with the amount of Target molecule in the mixture being assayed. Alternatively, the Nucleic acid ligand and the oligonucleotide constitute an energy transfer pair. For example, one member of the pair will be labeled with tetramethyl-rhodamine and the other will be fluorescein labeled. The fluoresceinbased fluorescence of such a complex is quenched when illuminated with blue light, as the green light emitted by the fluorescein will be absorbed by the tetramethylrhodamine group; the rhodamine-based fluorescence of this complex is not quenched Separation of the two halves of this energy transfer pair occurs upon Target molecule binding, and leads to a change in the emission profile at such sites on the Biochip. The displacement of the tetramethylrhodamine labeled molecule will lead to the sudden appearance of fluorescein-based fluorescence at this site on the Biochip, with the concomitant loss of rhodamine-based fluorescence. The simultaneous change in two different emission profiles will enable ratiometric imaging of each site to be performed, allowing sensitive measurement of Target molecule binding. It is clear to those skilled in the art that any energy transfer pair can be used in this embodiment, providing that they have appropriately matched excitation and emission spectra.

In an alternative embodiment, the displaced Nucleic acid is conjugated to one member of an affinity pair, such as biotin. A detectable molecule is then conjugated to the other member of the affinity pair, for example avidin. After the Test mixture is applied to the Biochip, the conjugated detectable molecule is added. The amount of detectable molecule at each site on the Biochip will vary inversely with the amount of Target molecule present in the Test mixture. In another embodiment, the displaced Nucleic acid will be biotin labeled, and can be detected by addition of fluorescently labeled avidin; the avidin itself will then be linked to another fluorescently labeled, biotin-conjugated compound. The biotin group on the displaced oligonucleotide can also be used to bind an avidin-linked reporter enzyme; the enzyme will then catalyze a reaction leading to the deposition of a detectable compound. Alternatively, the reporter enzyme will catalyze the production of an insoluble product that will locally quench the fluorescence of an intrinsically-fluorescent Biochip. In another embodiment of the displacement assay, the displaced oligonucleotide will be labelled with an immunologically-detectable probe, such as digoxigenin. The displaced oligonucleotide will then be bound by a first set of antibodies that specifically recognize the probe. These first antibodies will then be recognized and bound by a second set of antibodies that are fluorescently labeled or conjugated to a reporter enzyme. Many variations on these examples are well known to those skilled in the art.

In variations of the preceding embodiments, the Nucleic acid ligand will not contain a constant sequence region as described above. In these embodiments, the oligonucleotide will have a sequence that is complementary to all, or part of, the Nucleic acid ligand. Thus, each Nucleic acid ligand will bind an oligonucleotide with a unique sequence. The oligonucleotides can be displaced from Biochip-localized Nucleic acid ligands as described above upon Target binding. Alternatively, the oligonucleotides will be localized to specific locations on the Biochip as described above, which will in turn result in the specific localization of Nucleic acid ligands by complementary base-pairing to the oligonucleotides. Target molecule binding will displace the Nucleic acid ligand from the Biochip in this case, as described above. In each case, the oligonucleotide and/or the Nucleic acid ligand will be labeled as described above.

In other embodiments, Nucleic acid ligands will be localized to specific regions of the Biochip. Following contacting with the text mixture, the Biochip will then be contacted with a solution containing either (i) oligonucleotide with sequence complementary to the constant region of the Nucleic acid ligand; or (ii) oligonucleotides with sequence complementary to all or part of each Nucleic acid ligand, which ligand does not contain a constant sequence region as described above in this section. In these cases, binding of Target will prevent the subsequent binding of oligonucleotide. Again, the oligonucleotide and the Nucleic acid ligand can be labeled as described above in this section to monitor the binding of oligonucleotide.

Figure 4:
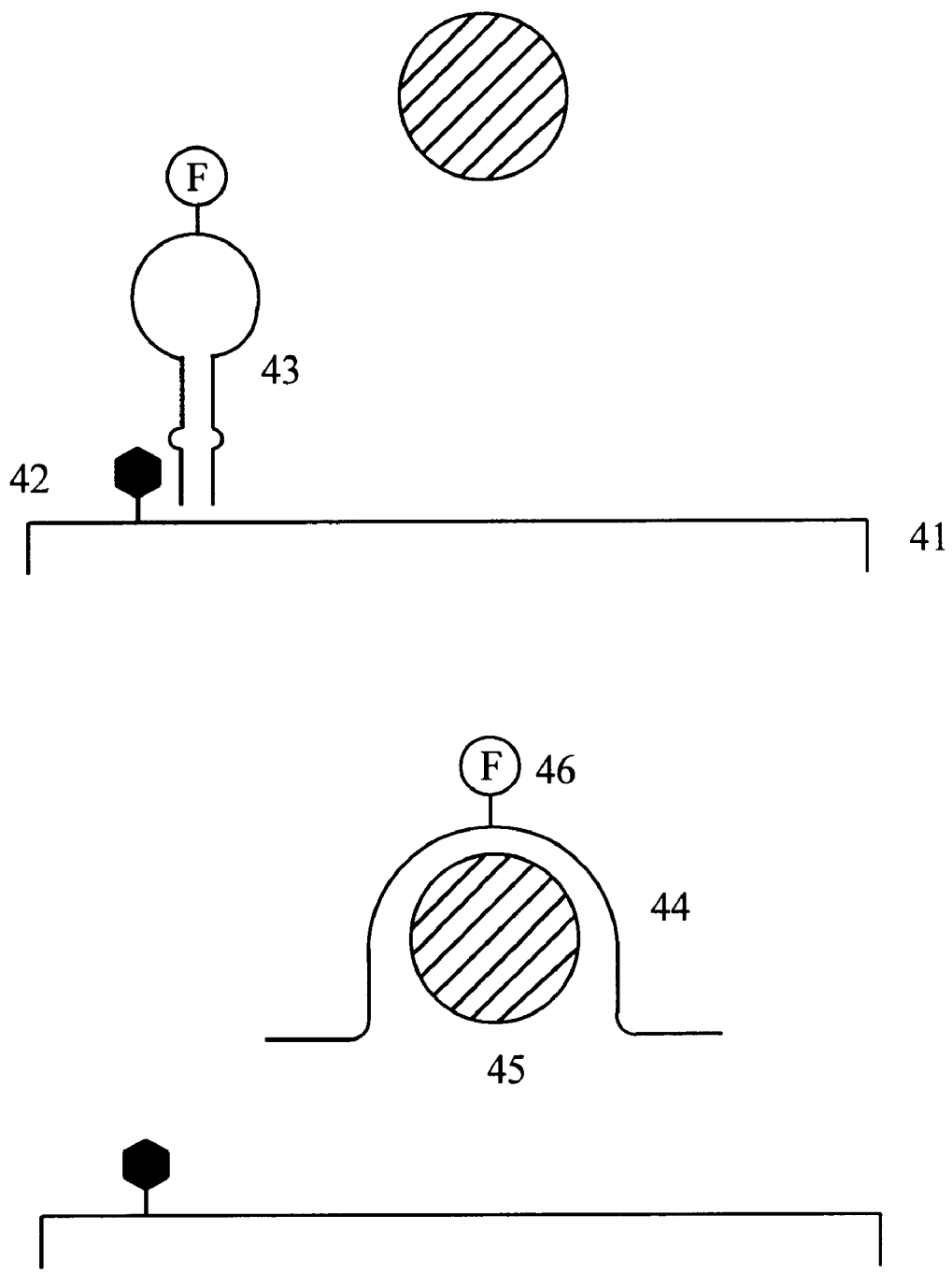
FIG. 4 shows a mechanism for detection in which a small molecule is bound to the surface of the Biochip, and the Nucleic acid ligands incorporate a binding site for this molecule.

C. Incorporation of Small Molecule Binding Sites into Nucleic Acid Ligands to Facilitate Target Molecule Binding In another embodiment, SELEX will be performed using a pool of Nucleic acids containing a binding site for a particular small molecule. An example of such a small molecule is the caffeine analogue theophylline. Single stranded Nucleic acid ligands against this molecule form a double-stranded stem with a hairpin loop in which the 5' and 3' ends of the molecule are close to one another. This structure only forms in the presence of theophylline. In this embodiment, a candidate mixture of theophylline ligands will be synthesized with random sequence in the hairpin loop. region, and the candidates will then be passed over a solid support, preferably a column, to which theophylline has been attached. The candidate ligands will bind tightly to theophylline, and will become immobilized on the column. The mixture containing Target molecules will be added to the column, and ligands that are eluted will be collected. This will select for ligands that bind their Target molecules in such a way that the ligand will no longer bind to theophylline. Such ligands will be displaced because the adoption of the structure that binds the Target molecule will disrupt the structure that binds the theophylline. The ligands will be refined in the standard ways described in the SELEX patent applications. A Biochip (FIG. 4) will then be fabricated (41) on which theophylline (42) is attached by any of the methods known in the art One or more individual species of the Nucleic acid ligands (43) will then be attached at defined locations on the Biochip, where they bind tightly to the theophylline. Contacting of the Test mixture with the Biochip leads to the displacement (44) from the Biochip of Nucleic acid ligands that bind to their cognate Target molecule (45). The displacement will be detected by any of the means detailed above (46). This technique will be used with any Nucleic acid ligand that forms a hairpin-type structure similar to theophylline, or any other Nucleic acid ligand that can be synthesized with additional random sequence, and will then bind to two different compounds in a mutually exclusive manner, such that the binding of one compound will displace the other.

Figure 5:
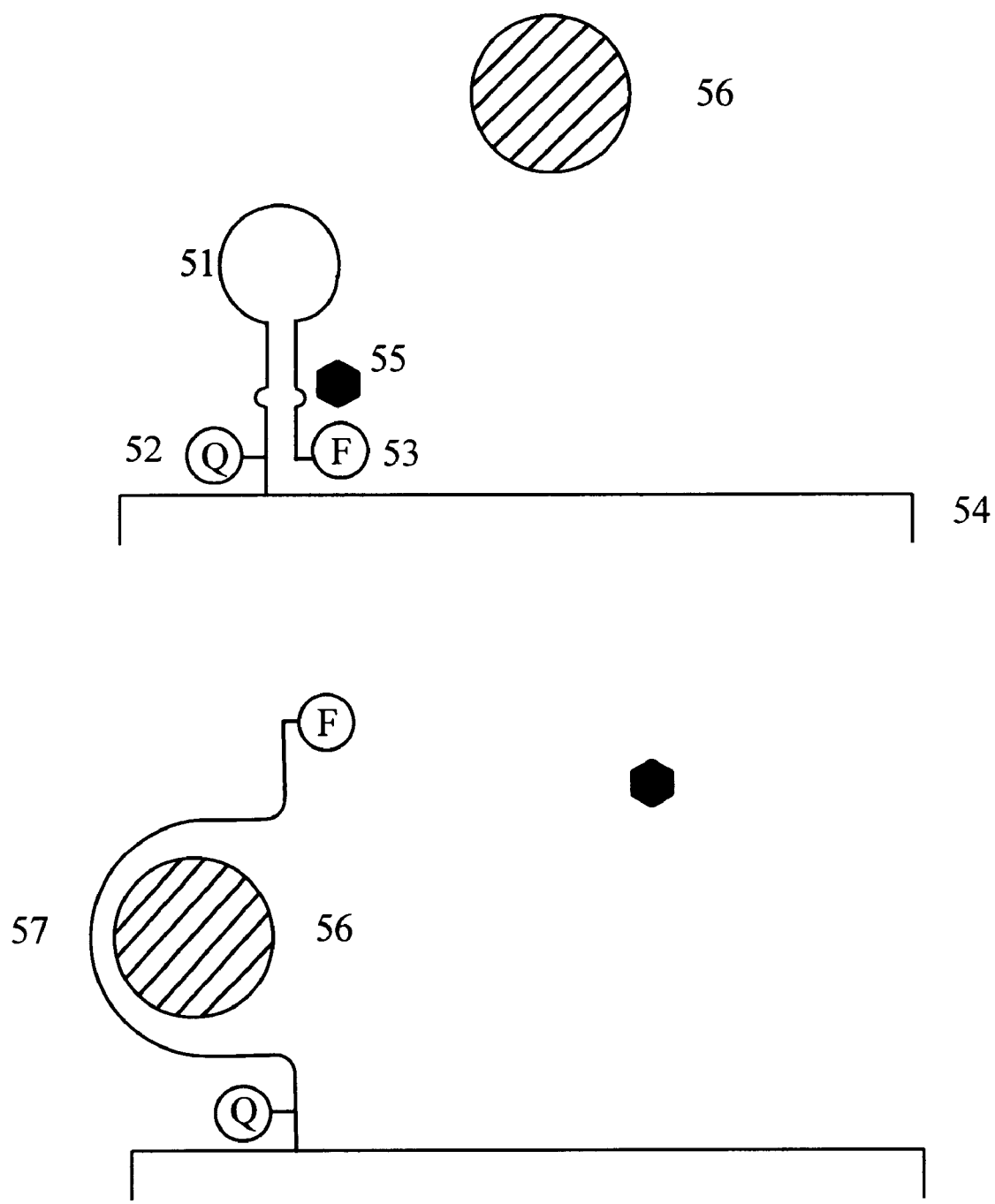
FIG. 5 depicts a mechanism for detection of target molecule binding in which a Nucleic acid ligand containing an additional binding site for a small molecule is immobilized on a Biochip.

In a related embodiment (FIG. 5), Nucleic acid ligands containing a binding site for a particular small molecule, such as theophylline, and a randomized segment will be synthesized as described in the above paragraph. The ligands (51) will also be labeled with both members of an energy transfer pair (52,53), such that in the presence of the small molecule, these groups are close to one another, and fluorescence is quenched. The ligands will then be deposited at specific regions of the Biochip (54), and the small molecule (55) will be added to the Biochip. The ligands will adopt the structure that binds the small molecule, and fluorescence will be quenched. The Test mixture will then be added to the Biochip, and Target molecules (56) will displace the small molecule from the appropriate Nucleic acid ligands. In order to bind the Target molecules, the Nucleic acid ligands will undergo a conformational change in which the two halves of the energy transfer pair are no longer next to one another (57). This will result in a change in the fluorescence profile at each site on the Biochip where a Target molecule has been bound. This embodiment will also be used for ligands that contain a binding for any small molecule, provided that such ligands undergo a conformational change upon displacement of the small molecule by the Target molecule.

A different displacement scheme will use the Target-molecule-dependent displacement of a labeled single-stranded DNA-binding protein from a support bound Nucleic acid ligand.

McGall et al., supra, suggest a technique for simultaneously identifying multiple Target Nucleic acid sequences using multiple probes. In the method contemplated, a first set of labeled probes against specific Targets is synthesized, with each probe containing an additional sequence that is unique for that particular probe. These unique sequences are complementary to a second set of oligonucleotides immobilized on a Biochip. The authors envision contacting the Target and the first set of probes in solution, then adding the complexes formed to the Biochip. The additional unique sequence region of each probe will localize that complex to a specific address on the Biochip via its interaction with the second probe bound at that site. Because there are methods known in the art that can be used to partition bound Nucleic acid ligand from unbound, this technique can be applied to the instant invention. Specifically, Nucleic acid ligands will be synthesized with an additional sequence that will be different for each species of Nucleic acid ligand and will preferably be distant from the residues important for the specific binding interaction. The Biochip will contain oligonucleotides with sequence complementary to the unique region of each Nucleic acid ligand species. Each Nucleic acid ligand will also have a detectable group, such as a fluorophore and/or a means for linking the Nucleic acid ligand to another detectable molecule as described above. Alternatively, the second set of Biochip-localized Nucleic acids and the Nucleic acid ligands themselves can be labeled in such a way that they form an energy transfer pair, as described above.

D. Detection of Binding Through a Signal-Amplifying Hybridization Cascade

Another series of embodiments of the instant invention will involve the use of a set of mutually-complementary Nucleic acids. In all the methods, the Nucleic acid ligand binds to a Target molecule whereupon the Nucleic acid ligand undergoes a conformational change that allows other Nucleic acids to hybridize thereto. The Nucleic acids that hybridize to the Target-bound Nucleic acid ligand also undergo a conformational change during hybridization that similarly allows other Nucleic acids to hybridize thereto. This chain reaction of conformational change and hybridization will continue, forming an increasingly large intermolecular hybridization complex at each site on the Biochip where a Nucleic acid ligand binds to a Target molecule. Any Nucleic acid structure that undergoes a hybridization-promoting conformational change upon (i) binding to a Target molecule, and/or (ii) hybridizing to another Nucleic acid, is suitable for use in this embodiment The use of cascade hybridization is described in the commonly assigned application entitled "System for Amplifying Fluorescent Signal Through Hybridization Cascade" filed Dec. 15, 1997 and specifically incorporated herein by reference.

Figure 6:
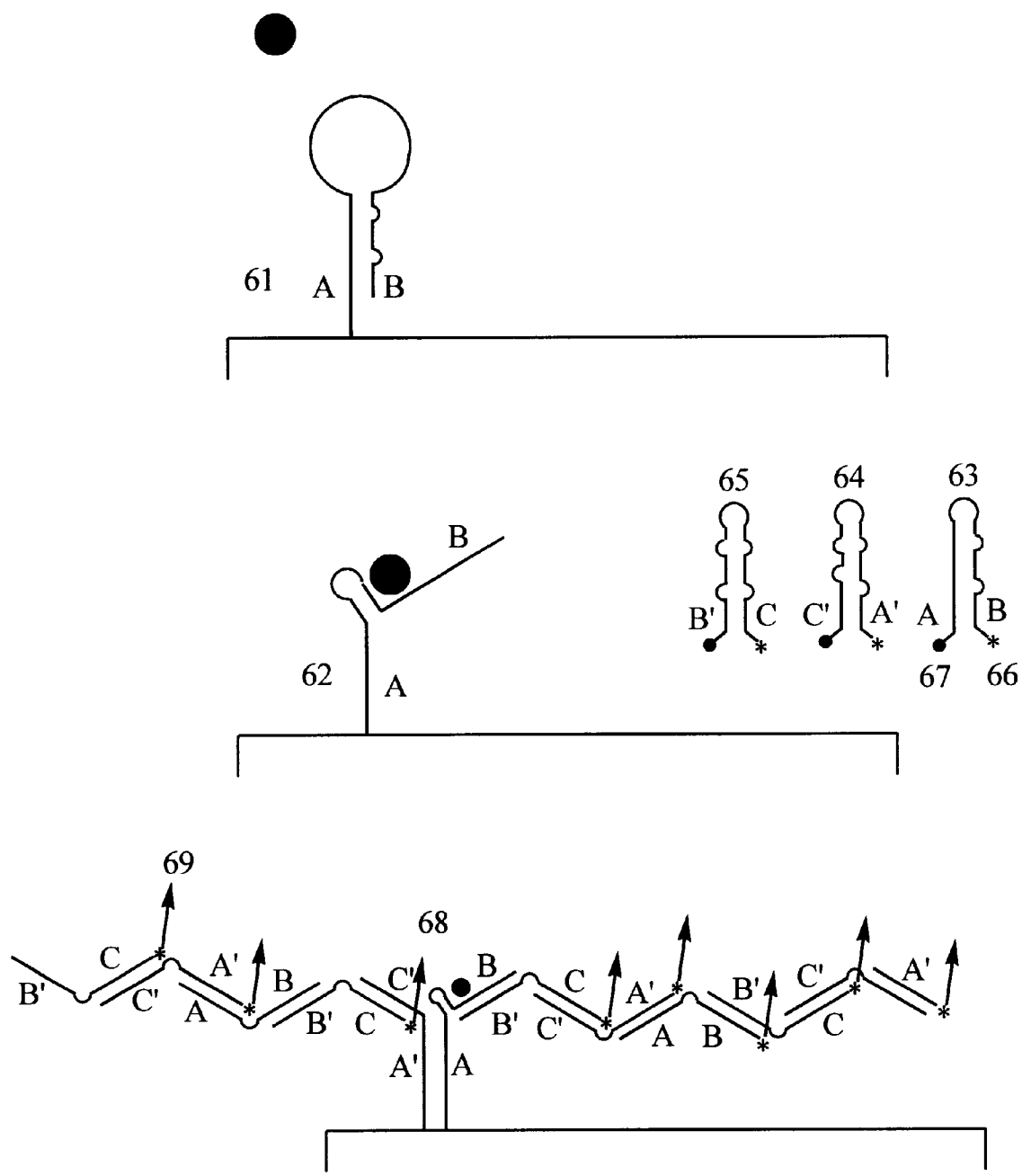
FIG. 6 depicts a detection system that uses a cascade of Nucleic acid hybridization.

The hybridizing Nucleic acids will be labeled with a fluorescent group and a quenching group at positions that are spatially adjacent only when the Nucleic acid is not participating in a hybridization reaction. Therefore, the formation of the intermolecular complex will be accompanied by the generation of an increasing large fluorescent signal at each site on the Biochip where a Target molecule binds to a Nucleic acid ligand. This signal can be detected by any of the fluorescence techniques known in the art In a preferred embodiment, a set of mutually-complementary stem-loop Nucleic acids will be synthesized. A Nucleic acid ligand will be designed with a stem-loop structure, in which the Target molecule binding site is located in the loop region. Each said species of Nucleic acid ligand will be immobilized at discrete locations on the Biochip. The stem region will comprise two partially complementary "arms" of sequence A and B (FIG. 6) that can undergo limited pairing to form an imperfect intramolecular double helix (61). This Nucleic acid ligand will undergo a structural change upon Target molecule binding such that the stem region is completely disrupted (62). Three or more further sets of imperfect stem-loop Nucleic acids will also be synthesized. The first further set will be identical to the Biochip-bound Nucleic acid ligand, but will not contain the Target molecule binding site in the loop region (63). The sequences of the stem regions of the latter two sets are represented as C'/A' (64) and B'/C (65), and are chosen so that they can bind perfectly to (i) one of the arms of the Nucleic acid ligand stem (A' pairs perfectly with A, and B' pairs perfectly with B), and (ii) the arms of the second set can bind perfectly to the arms of the third set (C' pairs perfectly with C). The three sets will further comprise a fluorescent group (66) and a quenching group (67) located at positions that are spatially adjacent only when the imperfect stem structure is formed. A Biochip with the stem-loop Nucleic acid ligands will be contacted with a Test mixture, and Target molecule binding will lead to the disruption of the stem region of said Nucleic acid ligands. Both sequences A and B will be available for base-pairing. The Biochip will then be contacted with a solution of all three sets of Nucleic acids. The arms of the stems of these latter Nucleic acids will then hybridize to any Nucleic acid ligand that has undergone a Target-binding reaction (68). Upon binding to the Nucleic acid ligand arms, the stem regions of the second and third set of Nucleic acids will be similarly disrupted, and the unhybridized arms can then hybridize to their complementary sequences. This process is driven by the favorable free energy difference between imperfect and the perfect double helices, and will continue until one of the Nucleic acids is depleted from the solution phase. At each hybridization step, another arm sequence becomes available for complementary base pairing, leading to the ultimate formation of a multimolecular complex of intermolecular double helices. Each hybridization step is accompanied by the spatial separation of the quenching group from the fluorescent group, resulting in a highly fluorescent signal (69) being generated at the site on the Biochip where a single Target molecule originally bound to a single Nucleic acid ligand. In this embodiment, the original fluorescent signal is highly amplified by the cascade of hybridization.

E. Direct Binding of Target Molecules to Spectroscopically Detectable Nucleic Acid Ligands In another embodiment, one or more spectroscopically detectable labeled Nucleic acid ligands will be immobilized on Biochips. The synthesis of such ligands is disclosed in Pittner et al U.S. Pat. No. 5,641,629 and U.S. Pat. No. 5,650,275, both of which are specifically incorporated herein by reference. The labels on such ligands undergo a detectable change in fluorescence intensity, fluorescence polarization or fluorescence lifetime upon binding of the Nucleic acid ligand to its Target molecule. Suitable labels include fluorescent labels (e.g. fluorescein, Texas Red), luminescent labels (e.g. luciferin, acridinium esters), energy transfer labels (e.g. fluorescein and tetramethylrhodamine), and near IR labels (e.g. dicyanines, La Jolla Blue dye). Binding of the Target molecule to the labeled ligand will be detected by measuring any change in fluorescence. These include, but are not limited to, changes in fluorescence polarization, fluorescence anisotropy, fluorescence intensity, and fluorescence lifetime. These measurements will be made continuously, or in a dynamic manner. Locations on the Biochip where a difference is detectable will then be known to have bound Target molecules, allowing the quantification of each Target molecule in the Test mixture.

In a preferred embodiment, Nucleic acid ligands bound to the Biochip will be labeled with one or more phosphorescent groups. These groups will be incorporated into the Nucleic acid ligand such that at least some of them are within the binding site of the Target molecule. The phosphorescent groups will be chosen from those known in the art so that they have an emission half life which is longer by a predetermined amount than the half life of non-specific binding of an inappropriate Target molecule to a Nucleic acid ligand. The medium in which the Biochip is incubated will contain a predetermined amount of a quenching agent that can effectively quench the phosphorescence. When Target molecule binds to a Nucleic acid ligand in a specific manner, then the phosphorescent groups will be protected from the quenching agents. If the Biochip is then illuminated with light of the appropriate wavelength, the phosphorescent groups of Nucleic acid ligands with specifically bound Target molecules will phosphoresce, and hence light will detected at sites on the Biochip where ligand is bound. The phosphorescence of Nucleic acid ligands that are unbound will be quenched, and so no light will be detected at such sites on the Biochip. The phosphorescence of Nucleic acid ligands that bind an inappropriate, non-cognate Target molecule will also be quenched, as the half life for the formation of these complexes will be much shorter than the emission half life of the phosphorescence groups. In other words, the individual phosphorescent groups in a non-specific complex will be many more times likely to encounter a quenching group in the solvent prior to photon emission than will those same groups in a specific complex. Any suitable phosphorescent group with an emission half life greater than the half life of formation of a specific Nucleic acid ligand-Target complex is contemplated in the present invention If the detection of phosphorescence is delayed by a predetermined amount of time following excitation illumination, then the phosphorescence signal can be distinguished from the background fluorescence signals, as these latter signals have a much shorter emission half life. This delay will also further enhance the specificity of detection, as only truly tightly bound Nucleic acid ligands will be protected from quenching. Furthermore, a series of phosphorescence images of the Biochip will be obtained, with optional brief washing of the Biochip between each exposure; the resulting series of images will then be integrated. This will enable non-specific signal to be further distinguished from non-specific signal, as the specific binding will persist between exposures, whereas the non-specific binding will not.

In another embodiment, the technique described in the preceding paragraph will be carried out using fluorescence groups on the Nucleic acid ligands, rather than phosphorescence groups.

F. Detection of Changes in Double-Helicity Accompanying Target Binding

In another embodiment, Target molecule binding will be assessed by monitoring changes in the degree of double-strandedness of each Nucleic acid ligand. It is known that Nucleic acid ligands undergo structural changes upon binding to Target, such as the formation, or expansion, of double stranded regions. In the instant invention, these changes will be detected by adding a fluorescent intercalating dye, such as ethidium bromide, to the Biochip, and measuring fluorescence levels at each location on the Biochip in the presence and absence of the Test mixture. A similar technique is suggested in Lockhart et al. (U.S. Pat. No. 5,556,752) for determining oligonucleotide probe hybridization to a Target Nucleic acid sequence.

G. Detection Through the use of Interferometry

In another embodiment, Target molecule binding will be detected by the use of an interferometric sensing system. A suitable system is described in Lin et al., Science 278: 840–842 (1997). Nucleic acid ligands will be attached to a microporous Biochip surface. Illumination of this surface with white light produces an interference pattern This results from light being reflected from the top and bottom of the porous Biochip surface. Interaction of a Target molecule with a Nucleic acid ligand locally alters the refractive index of the Biochip surface, and this in turn locally alters the wavelength of the interference fringe pattern. This can be measured by, for example, a charge coupled device camera H. Detection of Covalently Bound Target Molecules In another embodiment, methods known in the art that allow for the synthesis of Nucleic acid ligands containing one or more photoreactive groups, such as iodouridine, will be used. These ligands are capable of binding to their Target, and then becoming covalently attached to the Target upon photoactivation of the reactive group with light of the appropriate wavelength. An array of photoreactive ligands will be attached to a Biochip, and then contacted with the Test mixture. Photoactivation of the chip will covalently localize each Target molecule to its specific location on the chip. The covalently bound Target molecules can be detected by a sandwich assay, or with fluorescent protein dyes as described in the above section entitled "Generic Detection Techniques". Alternatively, the covalently associated complexes on the Biochip will be contacted with oligonucleotides complementary to all, or part of, the sequence of the Nucleic acid ligand. Nucleic acid ligands that are covalently bound to Target will not be able to hybridize to the complementary oligonucleotide. The complementary oligonucleotides will be labeled by any of the methods known in the art, as described above, to facilitate their detection.

V. Detection of Target Molecule Binding Through Methods That Do Not Involve Fluorescence Although preferred embodiments utilize fluorescent and phosphorescent detection techniques for determining Target molecule binding, there are other methods known in the art that have utility in this application.

A. Chemical Field Effect Transistors

Chemical Field effect transistor (CHEM-FET) technology exploits the local change in chemical potential that is created upon the binding of Target molecule to its ligand In this technology, an insulative silica "gate" is placed between two n-type semiconductors, forming a Biochip. Current will flow from one semiconductor to the other when a conducting channel is formed in the gate and a potential difference is applied. Such channels will be opened when an ionic species binds to the silica gate (Schenk et al. U.S. Pat. No. 4,238, 757). In another method (Lowe et al., U.S. Pat. No. 4,562, 157), ligands are bound to discrete regions of one of the semiconductors via photoactivation of derivatizing groups. The Biochip is then contacted with a mixture containing Target molecules. Binding of a Target molecule to a ligand leads to a net loss or gain of ions at that location of the Biochip. The ions locally alter the conductance at this location, which in turn leads to a change in the drain current in this area of the Biochip. If the Biochip is configured in such a way that current drains will be measured in discrete locations on the Biochip (multigated CHEM-FET), then spatial and quantitative assessment of Target binding will be achieved. Advances in the art should permit the scaling up of this technology to independently and accurately measure thousands of spatially discrete changes in drain current.

Another bioelectric change that can be measured using CHEM-FET is the photo-induced electron transfer which occurs in double-stranded DNA (Murphy et al. 1993. Science 262:1025–1029). As mentioned above, the degree of double-strandedness of each Nucleic acid ligand may change when a Target molecule is bound. Changes in the extent of double-helicity will lead to localized changes in drain currents in a CHEM-FET Biochip that is being illuminated. If the CHEM-FET Biochip is read before and after contact with the Target mixture, then detecting these differences will reveal the sites and extent of Target molecule binding.

B. Detection Through Surface Plasma Resonance

In a preferred embodiment, Target molecule binding will be detected through surface plasma resonance (SPR). In this technique, Nucleic acid ligand is immobilized on a gold or silver film on the surface of a prism; the metal film is then incubated in the appropriate liquid medium. Therefore, the metal film is at the prism-liquid interface. Light is directed through the prism towards the medium, and above a critical angle, total internal reflection of the light occurs. Above this critical angle, an evanescent wave extends into the medium by a distance that is approximately equal to the wavelength of the incident light. The evanescent wave excites free oscillating electrons, termed surface plasmons, in the metal film, and causes them to resonate. Energy is absorbed from the evanescent wave by the electrons during this process, thereby reducing the intensity of the internally reflected light. The angle at which total internal reflection, and hence resonance, occurs is exquisitively sensitive to changes in the refractive index of the medium immediately adjacent to the metal film. When a Target molecule binds to a Nucleic acid ligand on the surface of the film, the refractive index at this site changes, and the angle needed to cause resonance changes also. Thus in order to detect Target molecule binding, a detector system is arranged in which the angle of incident light is varied, and the intensity of the reflected light is measured. Resonance occurs when the intensity of the reflected light is at a minimum. Measuring the change in angle of incident light needed to bring about resonance at specific sites on the film in the presence of a Test mixture can then yield information about where a binding reaction has occurred on the surface of the film. A device for measuring SPR called BIAcore® is commercially available from Pharmacia Biosensors.

C. Detection Through the Use of Mass Spectroscopy

In another embodiment, the formation of Nucleic acid ligand-Target complex will be detected by mass spectroscopy. The surface of the Biochip will be irradiated in a spatially restricted and sequential way using a laser that is capable of ionizing the biological material on the Biochip. The mass of the ionization products will be detected by mass spectroscopy, and comparison with the mass of ionization products of the same unbound ligands will reveal where Target is bound. This technique is known in the art as Matrix Absorption/Laser Desorption and Ionization (MALDI) Time of Flight Mass Spectroscopy. The Nucleic acid ligands and the Targets in this embodiment can be covalently associated through the use of photoactivatable crosslinking groups on the Nucleic acid ligand, as described above in the section entitled "Detection of Covalently Bound Target Molecules".

D. Detection Through Atomic Force Microscopy (AFM) and Scanning-Tunneling Microscopy (STM)

These related methods are well known in the art as techniques useful for describing the topology of surfaces at the nanometer level. Hence, advances in these techniques will make them suitable for detecting sites on a Biochip where Target molecule has been bound by a Nucleic acid ligand.

Atomic force microscopy (AFM) uses a non-metallic probe which is scanned over the surface of interest, in this case a Biochip. The probe is moved close to the surface so that the probe is subject to electron-repulsive interactions with the material bound to the surface. Repulsion leads to the deflection of a cantilever upon which the probe is mounted, and this deflection is measured by a laser-photodiode detection system. The surface under examination is mounted on a stage, which stage is coupled to the deflection detection system by a computer. When the probe is deflected, the stage is lowered, allowing the probe to trace out a "contour map" of electron density for the surface. Using this technique,a reference map for a Nucleic acid Biochip in a buffer will be prepared. This will be compared with a map obtained from a Nucleic acid Biochip that has been incubated with a Test mixture. Comparison of the two maps will allow detection of sites on the Biochip where Target molecule has bound.

Scanning tunneling microscopy (STM uses a metallic probe which is scanned over a surface of interest. When the probe approaches the material bound to the surface, electrons can "tunnel" between the probe and the material, and the resulting current can be detected. The probe is scanned over the surface, and the vertical position of the probe is constantly varied to permit tunneling. This, as in AFM, gives a map of electron density, which map will be used as described in the above paragraph to detect Target molecule binding on a Nucleic acid ligand Biochip.

VI. Examples

A. Example One

Nucleic acid ligand GB41 was isolated from a SELEX experiment against the U251 glioma cell line, as described in U.S. patent application No. 08/434,425, filed May 3, 1995, entitled "Tissue SELEX". Here, the Nucleic acid ligand bears a 5' biotin and is immobilized to a streptavidin coated carboxylmethyl dextran Biochip surface (BIACORE 2000). The proteins are injected across flowcells containing GB41 or a version of GB41 in which the nucleotide sequence is scrambled. The scrambled sequence provides a test of binding specificity for the Nucleic acid ligand. Specific binding was detected to full-length tenascin and to a bacterially expressed protein representing fibronectin type m repeats 3–5, which comprises 12% of the mass of full-length tenascin. These proteins did not bind to the scrambled sequence oligonucleotide. The slow dissociation of full-length tenascin, a hexamer, may result form multivalent interactions on the surface. Experiments established the association and dissociation rate constants for this protein-Nucleic acid ligand interaction The association phase (0–125 sec) was linear due to the large size (1.2 million dalton) of tenascin, which causes slow diffusion into the dextran matrix (mass transport-limited binding). The slow dissociation (125–300 sec) was perhaps due to multivalent interactions that could form between the hexameric protein and the dextran-bound Nucleic acid ligand.

What is claimed is:

1. A method for making a biochip comprising a plurality of distinct nucleic acid ligands at spatially discrete locations on a solid support, the method comprising:
   I. identifying each of said distinct nucleic acid ligands to a target molecule by the method:
      (a) preparing a candidate mixture of nucleic acid sequences;
      (b) contacting said candidate mixture of nucleic acids with a target molecule, wherein nucleic acids having an increased affinity to said target molecule relative to the candidate mixture are partitioned from the remainder of the candidate mixture;
      (c) partitioning the increased affinity nucleic acids from the remainder of the candidate mixture;
      (d) amplifying the increased affinity nucleic acids to yield a mixture of nucleic acids enriched for nucleic acid sequences with relatively higher affinity and specificity for binding to said target molecule; and
      (e) repeating steps b), c) and d) until said nucleic acids possess the desired affinity for said target molecule, whereby a nucleic acid ligand of said target molecule may be identified;
   II. attaching said distinct nucleic acid ligands to spatially discrete locations on a solid support.

2. The method of claim 1 wherein said nucleic acid ligands are attached to said solid support via covalent bonds.

3. The method of claim 1 wherein said nucleic acid ligands are attached to said solid support via non-covalent bonds.

4. A method for making a plurality of solid supports each having a distinct nucleic acid ligand attached to its surface, the method comprising:
   I. Identifying each of said distinct nucleic acid ligands to a target molecule by the method:
      (a) preparing a candidate mixture of nucleic acid sequences;
      (b) contacting said candidate mixture of nucleic acids with a target molecule, wherein nucleic acids having an increased affinity to said target molecule relative to the candidate mixture are partitioned from the remainder of the candidate mixture;
      (c) partitioning the increased affinity nucleic acids from the remainder of the candidate mixture;
      (d) amplifying the increased affinity nucleic acids to yield a mixture of nucleic acids enriched for nucleic acid sequences with relatively higher affinity and specificity for binding to said target molecule; and
      (e) repeating steps b), c) and d) until said nucleic acids ligands possess the desired affinity for said target molecule, whereby a nucleic acid ligand of said target molecule may be identified;
   II. Attaching said distinct nucleic acid ligands to a plurality of solid supports.

* * * * *